(12) United States Patent
Takahashi

(10) Patent No.: US 8,206,382 B2
(45) Date of Patent: Jun. 26, 2012

(54) SURGICAL APPARATUS WITH SENSOR FOR OBTAINING STATES OF SURGICAL INSTRUMENT INFORMATION

(75) Inventor: Kazuhiko Takahashi, Hachioji (JP)

(73) Assignee: Olympus Medical Systems Corp. (JP)

( * ) Notice: Subject to any disclaimer, the term of this patent is extended or adjusted under 35 U.S.C. 154(b) by 910 days.

(21) Appl. No.: 12/212,731

(22) Filed: Sep. 18, 2008

(65) Prior Publication Data

US 2009/0018537 A1    Jan. 15, 2009

Related U.S. Application Data

(63) Continuation of application No. PCT/JP2007/055443, filed on Mar. 16, 2007.

(30) Foreign Application Priority Data

Mar. 22, 2006 (JP) ................................. 2006-078350

(51) Int. Cl.
*A61B 18/04* (2006.01)
(52) U.S. Cl. ........................................................ 606/34
(58) Field of Classification Search .................... 606/34, 606/41, 35, 36, 37, 38, 39, 40
See application file for complete search history.

(56) References Cited

U.S. PATENT DOCUMENTS

| | | | |
|---|---|---|---|
| 5,122,137 A | 6/1992 | Lennox | |
| 6,517,538 B1 | 2/2003 | Jacob et al. | |
| 2002/0077627 A1* | 6/2002 | Johnson et al. | 606/41 |
| 2002/0128643 A1* | 9/2002 | Simpson et al. | 606/34 |
| 2005/0131390 A1 | 6/2005 | Heinrich et al. | |

FOREIGN PATENT DOCUMENTS

| | | |
|---|---|---|
| JP | 57-110230 | 7/1982 |
| JP | 57-117825 | 7/1982 |
| JP | 58-69527 | 4/1983 |
| JP | 60-55925 | 4/1985 |
| JP | 60-77731 | 5/1985 |
| JP | 60-83634 | 5/1985 |
| JP | 61-10646 | 4/1986 |
| JP | 06-142113 | 5/1994 |
| JP | 10-052411 | 2/1998 |
| JP | 2000-227367 | 8/2000 |
| JP | 2001-037776 | 2/2001 |
| JP | 3210664 | 7/2001 |
| WO | WO 91/16859 | 11/1991 |

OTHER PUBLICATIONS

Search Report issued by European Patent Office in connection with corresponding European application No. EP 07 73 8888 on May 24, 2011.

Office Action issued by the Chinese Patent Office on Feb. 5, 2010 in connection with corresponding Chinese Patent Application No. 20078001054.7.

(Continued)

*Primary Examiner* — Kevin C Sirmons
*Assistant Examiner* — Brandy C Scott
(74) *Attorney, Agent, or Firm* — Ostrolenk Faber LLP

(57) ABSTRACT

A surgical apparatus has a surgical instrument to treat a diseased part of a patient. An energy supply unit supplies energy for driving the surgical instrument. A sensor obtains information about states of the surgical instrument. An energy change detector detects whether magnitude of energy supplied to the surgical instrument is changed or not. A control unit controls driving of the sensor, based on a result of detection by the energy change detector.

8 Claims, 5 Drawing Sheets

OTHER PUBLICATIONS

Translation of Office Action issued by the Chinese Patent Office on Feb. 5, 2010 in connection with corresponding Chinese Patent Application No. 20078001054.7.

International Search Report and Written Opinion mailed Jun. 12, 2007 in corresponding PCT International Application No. PCT/JP2007/055443.

Office Action issued by the Japanese Patent Office on Jul. 26, 2011 in connection with corresponding Japanese Patent Application No. 2006-078350.

English translation of Japanese Office Action issued in connection with Japanese Patent Application No. 2006-078350 on Jul. 26, 2011.

* cited by examiner

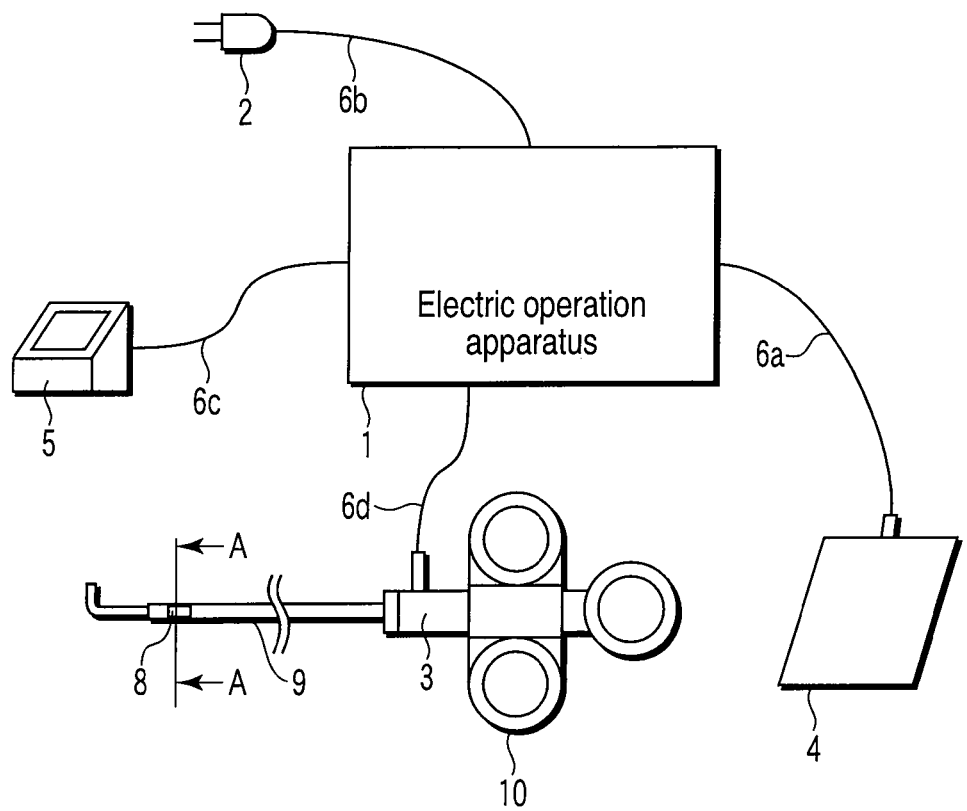
F I G. 1
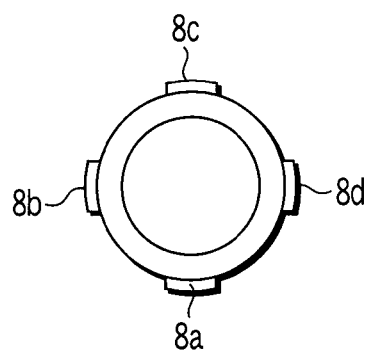
F I G. 2

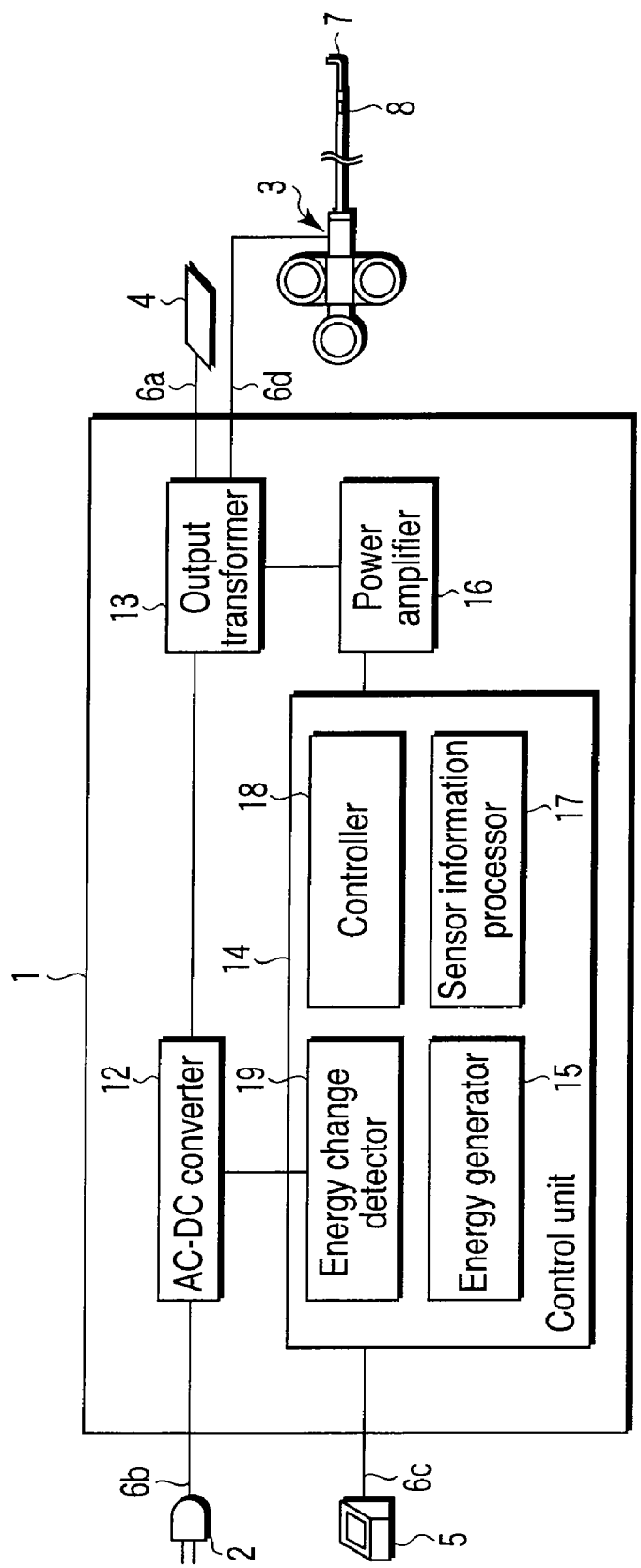
F I G. 3

SURGICAL APPARATUS WITH SENSOR FOR OBTAINING STATES OF SURGICAL INSTRUMENT INFORMATION

CROSS REFERENCE TO RELATED APPLICATIONS

This is a Continuation Application of PCT Application No. PCT/JP2007/055443, filed Mar. 16, 2007, which was published under PCT Article 21(2) in Japanese.

This application is based upon and claims the benefit of priority from prior Japanese Patent Application No. 2006-078350, filed Mar. 22, 2006, the entire contents of which are incorporated herein by reference.

BACKGROUND OF THE INVENTION

1. Field of the Invention

The present invention relates to a surgical apparatus having a sensor to obtain information about the states of a surgical instrument.

2. Description of the Related Art

Endoscopic surgery has been widely used because of its noninvasive feature without incising a patient's body mainly to approach a diseased organ. As a surgical instrument used in such an endoscopic surgery, there are energy instruments, such as a high-frequency surgical instrument and an electric scalpel, for cutting and coagulation by using a high-frequency wave or current. These energy instruments can control bleeding, and do not require a large force for cutting, and have been widely used for surgical operations including endoscopic surgery. Some of these energy instruments are provided with a sensor to obtain information about the states of a surgical instrument.

For example, Jpn. Pat. Appln. KOKAI Publication No. 2000-227367 discloses the technique in a master-slave operation system, in which an operation unit attached to a master arm detects the motion of the arm, detected signals are input to an electric scalpel and an arm drive, and an electric scalpel provided with a sensor using an optical fiber is driven to cut and remove a part of an diseased organ.

BRIEF SUMMARY OF THE INVENTION

According to a first aspect of the present invention, there is provided a surgical apparatus comprising:

a surgical instrument to treat a diseased part of a patient;

an energy supply unit to supply energy for driving the surgical instrument;

a sensor to obtain information about the states of the surgical instrument;

an energy change detector to detect whether magnitude of energy supplied to the surgical instrument is changed or not; and a control unit to control driving of the sensor, based on a result of detection by the energy change detector.

According to a second aspect of the present invention, there is provided a surgical apparatus, comprising a surgical instrument to treat a diseased part of a patient;

an energy supply unit to supply energy with a rectangular wave for driving the surgical instrument;

a sensor to obtain information about states of the surgical instrument;

an energy change detector to detect rising and falling of the rectangular wave energy supplied to the surgical instrument as an energy change point; and a control unit to control driving of the sensor, at positions other than the energy change point detected by the energy change detector.

BRIEF DESCRIPTION OF THE SEVERAL VIEWS OF THE DRAWING

FIG. 1 is a schematic diagram showing the configuration of an electric operation system according to an embodiment of the invention;

FIG. 2 is a sectional view taken along line A-A of an electric scalpel 3;

FIG. 3 is a diagram showing the internal configuration of an electric operation apparatus 1;

DETAILED DESCRIPTION OF THE INVENTION

Figure 4:
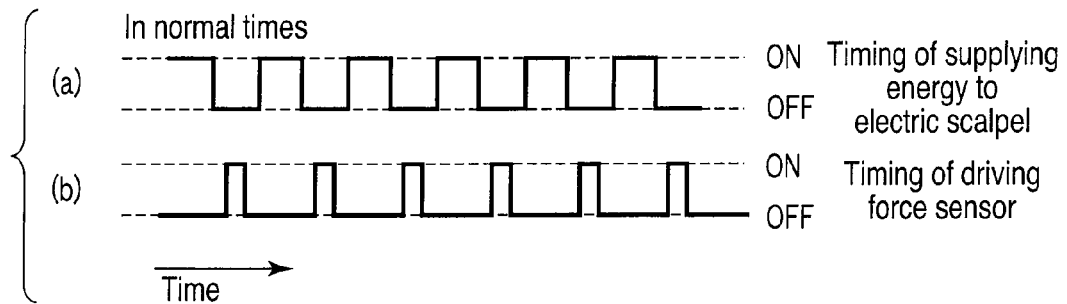
FIG. 4 shows the relationship (1) between the timing of energy supply to the electric scalpel 3 and the timing of driving a force sensor.

Hereinafter, embodiments of the invention will be explained in detail with reference to the accompanying drawings. FIG. 1 shows the configuration of an electric operation system according to an embodiment of the invention. An electric operation apparatus 1 is connected to a power cord 2, an electric scalpel 3 to make treatment for a patient based on high-frequency energy supplied from the electric operation apparatus 1, a patient plate 4 attached to the foot or back of a patient, and a foot switch 5 to input a high-frequency output instruction, through cords 6a to 6b. The distal end portion of the electric scalpel 3 is provided with an electrode 7. The electrode 7 is made of SUS 304, and is electrically conductive.

A force sensor 8 (here, a strain gauge) is affixed to a part of an insulating cover 9 of the electric scalpel 3, to detect the force applied to the distal end portion of the electric scalpel 3. FIG. 2 is a partial sectional view taken along line A-A of the electric scalpel 3 with the force sensor 8. The force sensor 8 is affixed in two or more directions to the electric scalpel 3, and detects the force applied to the electric scalpel 3 from two or more directions. The force sensor 8 is connected to the sensor information acquisition unit in the electric operation apparatus 1 through a not-shown cable.

FIG. 3 shows the internal configuration of the electric operation apparatus 1. An AC-DC converter 12 generates a DC voltage from a commercial power supply supplied through the power cord 2, and supplies the DC voltage to components of the electric operation apparatus 1. An output transformer 13 applies a voltage to en electrode 7 of the electric scalpel 3 and the patient plate 4. The output transformer is powered when the patient plate 4 is attached to the foot or back of a patient, and the electrode is attached to a diseased part of a patient. Areas close to the patient plate 4 and electrode 7 are heated. The patient plate 4 has a wide area, and is not heated high. In contrast, the electrode 7 has a small area, and is heated so high as to cauterize the tissue of a patient.

A control unit 14 includes an energy generator 15, an energy change detector 19, a sensor information processor 17, and a controller 18. The energy generator 15 generates high-frequency energy with a rectangular wave for high-frequency treatment. A power amplifier 16 amplifies the high-frequency energy generated by the energy generator 15. The sensor information processor 17 processes a signal detected by a force sensor 8, and detects the force applied to the distal end portion of the electric scalpel 3. The energy change detector 19 detects the rising and falling of a rectangular wave generated by the energy generator 15. The controller 18 controls the force sensor 8 not to be driven at positions other than the rising and falling positions of the rectangular wave energy generated by the energy generator 15 (the high-frequency energy ON and OFF periods as explained later).

FIGS. 4(*a*) and 4(*b*) show the relationship (1) between the timing of energy supply to the electric scalpel 3 and the timing of driving the force sensor 8. FIG. 4(*a*) shows the waveform (rectangular wave) of a high-frequency energy generated by the energy generator 15 and supplied to the electric scalpel 3. FIG. 4(*b*) shows the timing of driving the force sensor 8. In the examples of FIGS. 4(*a*) and 4(*b*), the force sensor 8 is driven during high-frequency energy OFF periods. The electric energy is stably supplied during these periods, a noise is not generated and not mixed into the sensor output.

Figure 5:
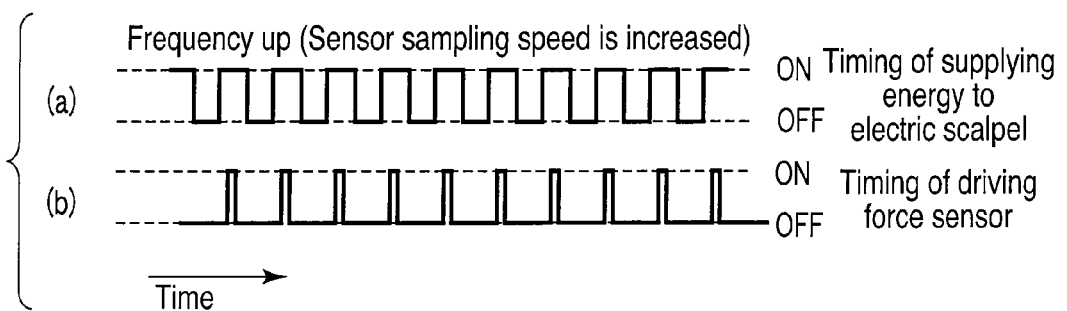
FIG. 5 shows the relationship (2) between the timing of energy supply to the electric scalpel 3 and the timing of driving a force sensor.

FIGS. 5(*a*) and 5(*b*) show the relationship (2) between the timing of energy supply to the electric scalpel 3 and the timing of driving the force sensor 8. FIG. 5(*a*) shows the waveform (rectangular wave) of the high-frequency energy generated by the energy generator 15 and supplied to the electric scalpel 3. FIG. 5(*b*) shows the timing of driving the force sensor 8. In these examples, the force sensor 8 is driven during high-frequency energy ON periods. The electric energy is stably supplied also during electric energy ON periods, the force sensor 8 can be driven at these periods. Further, FIGS. 5(*a*) and 5(*b*) show the timing of driving the force sensor 8 when the frequency of the high-frequency energy supplied to the electric scalpel 3 is increased. A sampling speed by the force sensor 8 is increased.

Figure 6:
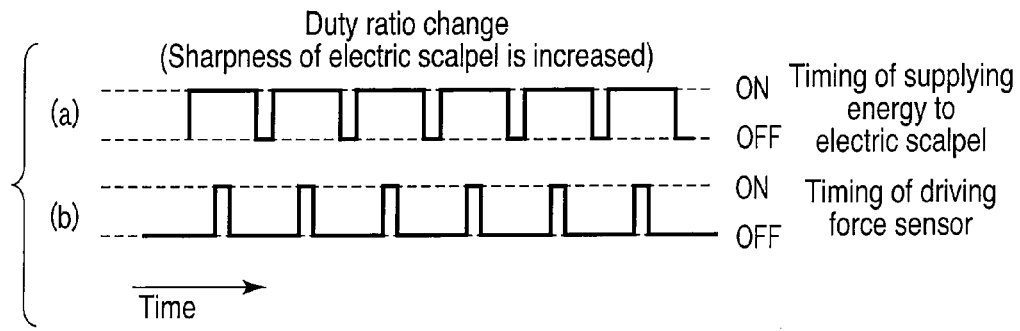
FIG. 6 shows the relationship (3) between the timing of energy supply to the electric scalpel 3 and the timing of driving a force sensor.

FIGS. 6(*a*) and 6(*b*) show the relationship (3) between the timing of energy supply to the electric scalpel 3 and the timing of driving the force sensor 8. FIG. 6(*a*) shows the waveform (rectangular wave) of the high-frequency energy generated by the energy generator 15 and supplied to the electric scalpel 3. FIG. 6(*b*) shows the timing of driving the force sensor 8. In these examples, the force sensor 8 is driven during high-frequency energy ON periods. Comparing with FIGS. 4(*a*) and 4(*b*), in FIGS. 6(*a*) and 6(*b*), the duty ratio is changed to prolong the ON period of the high-frequency energy supplied to the electric scalpel 3. This increases the sharpness of the electric scalpel.

Figure 7:
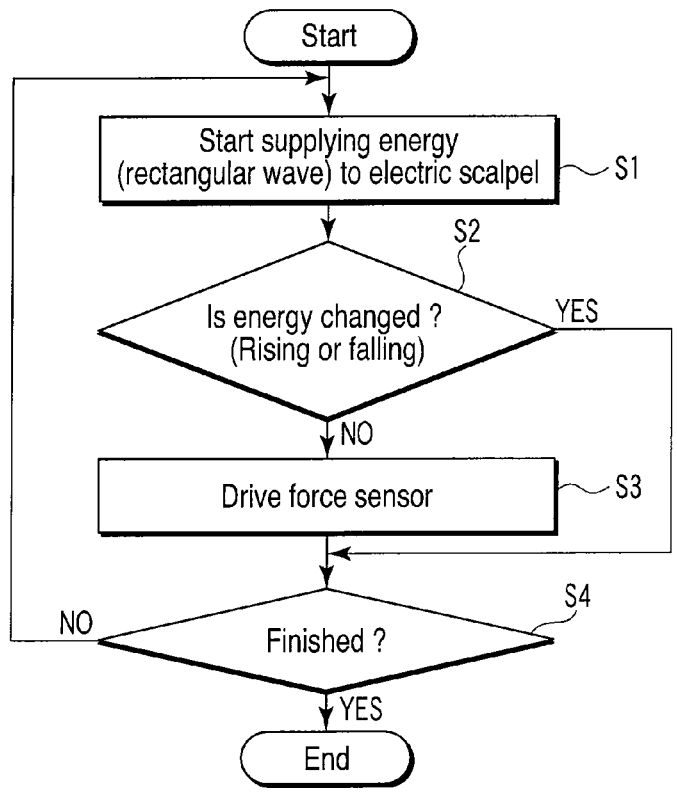
FIG. 7 is a flowchart for explaining a process to control driving of a force sensor 8 at the time of operation.

FIG. 7 is a flowchart for explaining the process to control driving of a force sensor 8 at the time of operation. First, an operator steps the foot switch 5 to issue an instruction to output high-frequency energy. The energy generator 15 generates high-frequency energy, and supplies the high-frequency energy to the electric scalpel 3 (step S1). In this embodiment, a rectangular wave is generated as high-frequency energy. Then, whether the rectangular wave energy is changed or not, or whether the rising or falling of the rectangular wave is detected or not, is judged (step S2). When NO in step S2, the rectangular wave energy is regarded as stable, and the force sensor 8 is driven (step S3). Then, whether the operation is finished or not is judged (step S4). When NO in step S4, the process returns to step S1. When the rising or falling of the rectangular wave is detected in the above step, YES in step S2. In this case, the process is shifted to step 4 without driving the force sensor 8.

Figure 8:
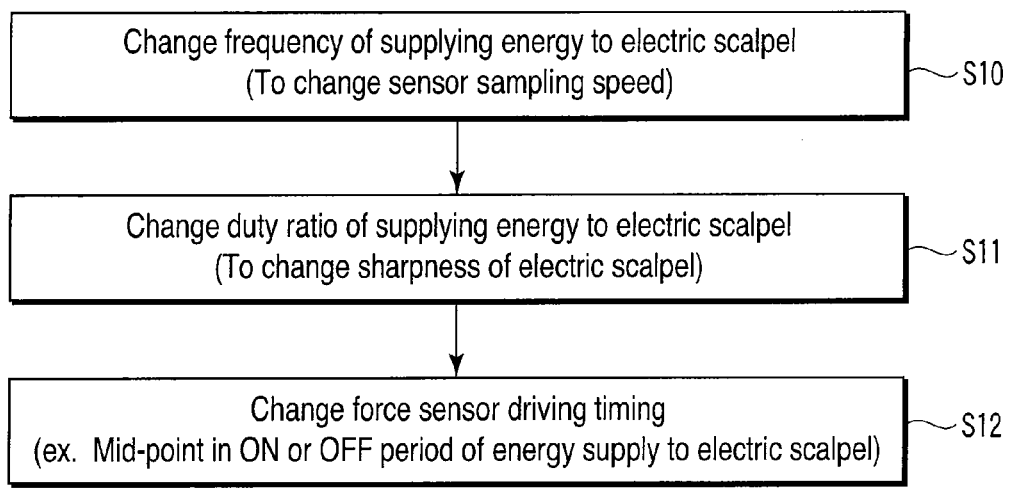
FIG. 8 is a flowchart showing a process to change the timing of driving a force sensor 8 according to variations in high-frequency energy supplied to an electric scalpel 3.

FIG. 8 is a flowchart showing the process of changing the timing of driving the force sensor 8 according to changes in the high-frequency energy supplied to the electric scalpel 3. First, the frequency of the energy supplied to the electric scalpel 3 is changed to change the sensor sampling speed (step S10). Then, the duty ratio of the energy supplied to the electric scalpel 3 to change the sharpness of the electric scalpel 3 (step S11). Then, the force sensor driving timing is changed according to the change in step S11. For example, the force sensor driving timing is changed to the mid point in the ON or OFF period of energy supply to the electric scalpel 3 (step S12).

An electric scalpel is used in this embodiment. However, other energy instruments such as an ultrasonic surgical instrument may be used. As for the sensor, other force detection sensors, such as an optical fiber sensor and a piezoelectric sensor, may be used.

In the embodiment described herein, the force sensor 8 is affixed to the electric scalpel 3. The force sensor 8 and electric scalpel 3 may be separated.

According to the embodiment described herein, the force sensor 7 is driven during ON or OFF periods with stable energy, other than during rising or falling with greatly changed high-frequency energy. This minimizes the influence upon the sensor output when an energy instrument is used.

According to the present invention, the influence upon the sensor output when an energy instrument is used can be minimized.

What is claimed is:

1. A surgical apparatus comprising:
a surgical instrument configured to treat a diseased part of a patient;
an energy supply unit configured to supply energy, having a waveform configured to turn on and off, for driving the surgical instrument;
a sensor configured to obtain information about states of the surgical instrument;
an energy change detector configured to detect rising and falling of the waveform of the energy supplied to the surgical instrument as an energy change point; and
a control unit configured to control the sensor to drive at positions other than the energy change point detected by the energy change detector,
wherein positions other than the energy change point are ON or OFF periods of the energy,
the control unit comprising:
a frequency change unit configured to change the frequency of the waveform of the energy;
a duty ratio change unit configured to change a duty ratio of the waveform of the energy; and
a drive timing control unit which drives the sensor in either an ON or OFF period of a wave having the frequency changed by the frequency change unit and either an ON or OFF period of a wave having the duty ratio changed by the duty ratio change unit.

2. The surgical apparatus according to claim 1, wherein the surgical instrument is a high-frequency surgical instrument or an electric surgical instrument.

3. The surgical apparatus according to claim 1, wherein the sensor is a force sensor to detect strains of the surgical instrument.

4. The surgical apparatus according to claim 1, wherein the sensor and energy instrument are combined in one piece.

5. The surgical apparatus according to claim 1, wherein the sensor and energy instrument are separated.

6. The surgical apparatus according to claim 1, wherein the energy has a rectangular waveform.

7. The surgical apparatus according to claim 1, wherein the drive timing control unit is configured to cause the sensor to drive in a mid point in the ON or OFF period of the waveform of the energy.

8. The surgical apparatus according to claim 1, wherein the control unit is configured to cause the frequency change unit to change the frequency of the waveform of the energy when the instrument is used, and causes the duty ratio change unit to change the duty ratio of the waveform of the energy so as to increase the energy supplied to the instrument when the instrument is used.

* * * * *